US00PP27959P3

(12) United States Plant Patent
Konst

(10) Patent No.: US PP27,959 P3
(45) Date of Patent: May 2, 2017

(54) ***ALSTROEMERIA* PLANT NAMED 'KONCASUNDA'**

(50) Latin Name: *Alstroemeria hybrida*
Varietal Denomination: Koncasunda

(71) Applicant: Johannes Wilhelmus Maria Konst, Nieuwveen (NL)

(72) Inventor: Johannes Wilhelmus Maria Konst, Nieuwveen (NL)

(73) Assignee: Konst Breeding B.V., Nieuwveen (NL)

( * ) Notice: Subject to any disclaimer, the term of this patent is extended or adjusted under 35 U.S.C. 154(b) by 41 days.

(21) Appl. No.: 14/756,180

(22) Filed: Aug. 12, 2015

(65) Prior Publication Data

US 2017/0049026 P1 Feb. 16, 2017

(51) Int. Cl.
*A01H 5/02* (2006.01)

(52) U.S. Cl.
USPC ..... Plt./309

(58) Field of Classification Search
USPC ..... Plt./309
See application file for complete search history.

*Primary Examiner* — Keith Robinson
(74) *Attorney, Agent, or Firm* — C. A. Whealy

(57) ABSTRACT

A new and distinct cultivar of *Alstroemeria* plant named 'Koncasunda', characterized by its compact and mounding plant habit; sturdy and strong plants; vigorous growth habit and rapid growth rate; freely branching habit; numerous light yellow-colored flowers; and good garden performance.

2 Drawing Sheets

Botanical designation: *Alstroemeria hybrida.*
Cultivar denomination: 'KONCASUNDA'.

BACKGROUND OF THE INVENTION

The present invention relates to a new and distinct cultivar of *Alstroemeria* plant, botanically known as *Alstroemeria hybrida*, typically grown as a container-type garden *Alstroemeria* and hereinafter referred to by the name 'Koncasunda'.

The new *Alstroemeria* plant is a product of a planned breeding program conducted by the Inventor in Nieuwveen, The Netherlands. The objective of the breeding program is to create new compact container-type garden *Alstroemeria* plants that have an early and freely flowering habit with attractive leaf and flower coloration.

The new *Alstroemeria* plant originated from a cross-pollination made by the Inventor in Nieuwveen, The Netherlands in June, 2010 of a proprietary selection of *Alstroemeria hybrida* identified as code designation 07-0-RD, not patented, as the female, or seed, parent with a proprietary selection of *Alstroemeria hybrida* identified as code designation 21604-1, not patented, as the male, or pollen, parent. The new *Alstroemeria* plant was discovered and selected by the Inventor as a single flowering plant from within the progeny of the stated cross-pollination in a controlled greenhouse environment in Nieuwveen, The Netherlands in June, 2012.

Asexual reproduction of the new *Alstroemeria* plant by in vitro rhizogenesis in a controlled greenhouse environment in Nieuwveen, The Netherlands since June, 2012 has shown that the unique features of this new *Alstroemeria* plant are stable and reproduced true to type in successive generations.

SUMMARY OF THE INVENTION

Plants of the new *Alstroemeria* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Koncasunda'. These characteristics in combination distinguish 'Koncasunda' as a new and distinct *Alstroemeria* plant:

1. Compact and mounding plant habit.
2. Sturdy and strong plants.
3. Vigorous growth habit and rapid growth rate.
4. Freely branching habit.
5. Numerous light yellow-colored flowers.
6. Good garden performance.

Plants of the new *Alstroemeria* can be compared to plants of the female parent selection. Plants of the new *Alstroemeria* differ primarily from plants of the female parent selection in flower color as plants of the female parent selection have red purple and yellow-colored flowers.

Plants of the new *Alstroemeria* can be compared to plants of the male parent selection. Plants of the new *Alstroemeria* differ primarily from plants of the male parent selection in flower color as plants of the male parent selection have light orange-colored flowers.

Plants of the new *Alstroemeria* can be compared to plants of the *Alstroemeria hybrida* 'Konesert', disclosed in U.S. Plant Pat. No. 20,030. In side-by-side comparisons conducted in Nieuwveen, The Netherlands, plants of the new *Alstroemeria* differed from plants of 'Konesert' in the following characteristics:

1. Plants of the new *Alstroemeria* were more compact than plants of 'Konesert'.
2. Plants of the new *Alstroemeria* were more freely flowering than plants of 'Konesert'.
3. Plants of the new *Alstroemeria* had larger flowers than plants of 'Konesert'.

4. Plants of the new *Alstroemeria* and 'Konesert' differed slightly in flower color.

BRIEF DESCRIPTION OF THE PHOTOGRAPHS

The accompanying colored photographs illustrate the overall appearance of the new *Alstroemeria* plant showing the colors as true as it is reasonably possible to obtain in colored reproductions of this type. Colors in the photographs may differ slightly from the color values cited in the detailed botanical description which accurately describe the colors of the new *Alstroemeria* plant.

The photograph on the first sheet is a side perspective view of a typical flowering plant of 'Koncasunda' grown in container.

The photograph on the second sheet is a close-up view of typical flowers of 'Koncasunda'.

DETAILED BOTANICAL DESCRIPTION

The aforementioned photographs and following observations and measurements describe plants of the new *Alstroemeria* grown during the winter and spring in 19-cm containers in a glass-covered greenhouse in Nieuwveen, The Netherlands and under cultural practices typical of commercial container-type *Alstroemeria* production. During the production of the plants, day temperatures ranged from 6° C. to 35° C. and night temperatures ranged from 6° C. to 20° C. Plants were 20 weeks old when the photographs and description were taken. In the following description, color references are made to The Royal Horticultural Society Colour Chart, 2001 Edition, except where general terms of ordinary dictionary significance are used.

Botanical classification: *Alstroemeria hybrida* 'Koncasunda'.

Parentage:

*Female, or seed, parent*.—Proprietary selection of *Alstroemeria hybrida* identified as code designation 07-0-RD, not patented.

*Male or pollen parent*.—Proprietary selection of *Alstroemeria hybrida* identified as code designation 21604-1, not patented.

Propagation:

*Type*.—In vitro rhizogenesis.

*Root description*.—Thick, fleshy; typically white in color, actual color of the roots is dependent on substrate composition, water quality, fertilizers, substrate temperature and physiological age of roots.

*Rooting habit*.—Freely branching; dense.

*Rhizome description*.—Shape: Elongate; rounded. Length: About 7.5 cm. Diameter: About 1 cm. Texture: Smooth. Color: Close to 161A.

Plant description:

*Plant and growth habit*.—Perennial garden plant; compact and mounded; freely branching habit, bushy appearance; sturdy and strong plants; vigorous growth habit; rapid growth rate.

*Plant height*.—About 20 cm.

*Plant diameter* (*area of spread*).—About 35 cm.

Stem description:

*Aspect*.—Mostly upright.

*Internode length*.—About 3 mm to 17 mm.

*Strength*.—Strong, sturdy.

*Texture*.—Smooth, glabrous.

*Color*.—Close to 144D strongly tinged with close to 187B.

Leaf description:

*Arrangement*.—Alternate; below the peduncle, arranged in a single whorl; leaves sessile.

*Length*.—About 3.9 cm to 10.1 cm.

*Width*.—About 1 cm to 1.8 cm.

*Shape*.—Lanceolate.

*Apex*.—Acute.

*Base*.—Attenuate.

*Margin*.—Entire.

*Texture, upper and lower surfaces*.—Smooth, glabrous.

*Venation pattern*.—Parallel.

*Color*.—Developing and fully expanded leaves, upper surface: Close to 137A; venation, close to 137C. Developing and fully expanded leaves, lower surface: Close to 137B; venation, close to 146B.

Flower description:

*Flower type and habit*.—Single cup-shaped flowers arranged in compound umbels; flowers face upright to outwardly; freely flowering habit with up to 15 flowers developing per inflorescence and about 50 to 90 flowers developing per plant during the flowering season.

*Natural flowering season*.—Flowering continuous from the late spring until the autumn in The Netherlands; early-flowering habit, plants begin flowering about 10 to 18 weeks after stem initiation.

*Fragrance*.—None detected.

*Flower longevity on the plant*.—About one to three weeks, longevity is temperature-dependent; flowers not persistent.

*Flower longevity as a cut flower*.—About one to two weeks, longevity is temperature-dependent; flowers not persistent.

*Flower buds*.—Length: About 5.5 cm. Diameter: About 8 mm. Shape: Ovoid. Color: Close to 2D and 39C to 39B; at the apex, close to 138A.

*Umbel height*.—About 8.7 cm.

*Umbel diameter*.—About 13 cm to 15 cm.

*Flower diameter*.—About 5.5 cm to 6.5 cm.

*Flower depth* (*height*).—About 6 cm to 6.5 cm.

*Perianth*.—Arrangement: Six arranged in two whorls, each whorl with two lateral and one median segments. Size, inner perianth: Length, lateral segments: About 6.5 cm. Width, lateral segments: About 1.8 cm. Length, median segment: About 6.2 cm. Width, median segment: About 1.8 cm. Size, outer perianth: Length, lateral segments: About 6.1 cm. Width, lateral segments: About 2.8 cm. Length, median segment: About 6.1 cm. Width, median segment: About 2.7 cm. Shape, inner perianth, lateral and median segments: Oblanceolate. Shape, outer perianth, lateral and median segments: Obovate. Apex, inner perianth, lateral and median segments: Acute. Apex, outer perianth, lateral and median segments: Emarginate, wishbone-shaped. Base, inner and outer perianths, lateral and median segments: Attenuate. Margin, inner and outer perianths, lateral and median segments: Mostly entire; towards the apex, crenulate. Texture, inner and outer perianths, lateral and median segments: Smooth, glabrous. Luster, inner and outer perianths, lateral and median segments: Matte, dull. Color, inner perianth: When opening, lateral segments, upper surface: Close to 14D; midsection, close to 5A; at the base, close to 144A; spots and stripes, close to 187A. When opening, lateral segments, lower surface: Close to 14D; mid-section, close to 2A; at the base, close to 144A; venation, close to 59A and 144A; spots and stripes, close to 187A. When opening, median segment, upper surface: Close to 14D; at the base, close to 144A; spots and stripes, close to 187A. When opening, median segment, lower surface: Close to 14D; at the base, close to 144A; venation, close to 59A and 144A; spots and stripes, close to 187A. Fully opened, lateral segments, upper surface: Close to 14D, and at the apex, close to 63C; mid-section, close to 5A; towards the base, close to 63D, and at the base, close to 144A; spots and stripes, close to 187A; color does not fade with development. Fully opened, lateral segments, lower surface: Close to 14D, and at the apex, close to 63C; mid-section, close to 2A; towards the base, close to 63D, and at the base, close to 144A; venation, close to 59A and 144A; spots and stripes, close to 187A; color does not fade with development. Fully opened, median segment, upper surface: Close to 14D; towards the base, close to 63D, and at the base, close to 144A; spots and stripes, close to 187A; color does not fade with development. Fully opened, median segment, lower surface: Close to 14D; at the base, close to 144A; venation, close to 59A and 144A; spots and stripes, close to 187A; color does not fade with development. Color, outer perianth: When opening, lateral and median segments, upper surface: Close to 2D, and at the apex, close to 144A; mid-section, close to 63B; at the base, close to 62D; spots and stripes, close to 61A. When opening, lateral and median segments, lower surface: Close to 2D, and at the apex, close to 144A; mid-section, close to 63B; at the base, close to 63D; venation, close to 144A. Fully opened, lateral and median segments, upper surface: Close to 2D, and at the apex, close to 144A; mid-section, close to 63B; at the base, close to 62D; spots and stripes, close to 61A; color does not fade with subsequent development. Fully opened, lateral and median segments, lower surface: Close to 2D, and at the apex, close to 144A; mid-section, close to 63B; at the base, close to 63D; venation, close to 144A; color does not fade with subsequent development.

*Pedicels*.—Length: About 0.7 cm to 1.3 cm. Diameter: About 1.5 mm to 3 mm. Strength: Strong. Angle: Erect to about 70° to 85° from vertical. Texture: Smooth, glabrous. Color, upper and lower surfaces: Close to 144D heavily tinged with close to 187B.

*Reproductive organs*.—Stamens: Quantity per flower: Six. Anther shape: Oval. Anther size: About 3 mm by 8 mm. Anther color: Close to 153B. Pollen amount: Scarce. Pollen color: Close to 153C. Pistils: Quantity per flower: One. Pistil length: About 4 cm. Style length: About 3.6 cm. Style color: Proximally, close to 73D; distally, close to 75C. Stigma color: Close to 11A. Ovary color: Close to 138A.

*Fruits and seeds*.—Fruit and seed development has not been observed on plants of the new *Alstroemeria*.

Disease & pest resistance: Plants of the new *Alstroemeria* have not been observed to be resistant to pathogens and pests common to *Alstroemeria* plants.

Garden performance: Plants of the new *Alstroemeria* have been observed to have good garden performance and to tolerate wind, rain and temperatures ranging from about 6° C. to about 35° C.

It is claimed:

1. A new and distinct *Alstroemeria* plant named 'Koncasunda' as illustrated and described.

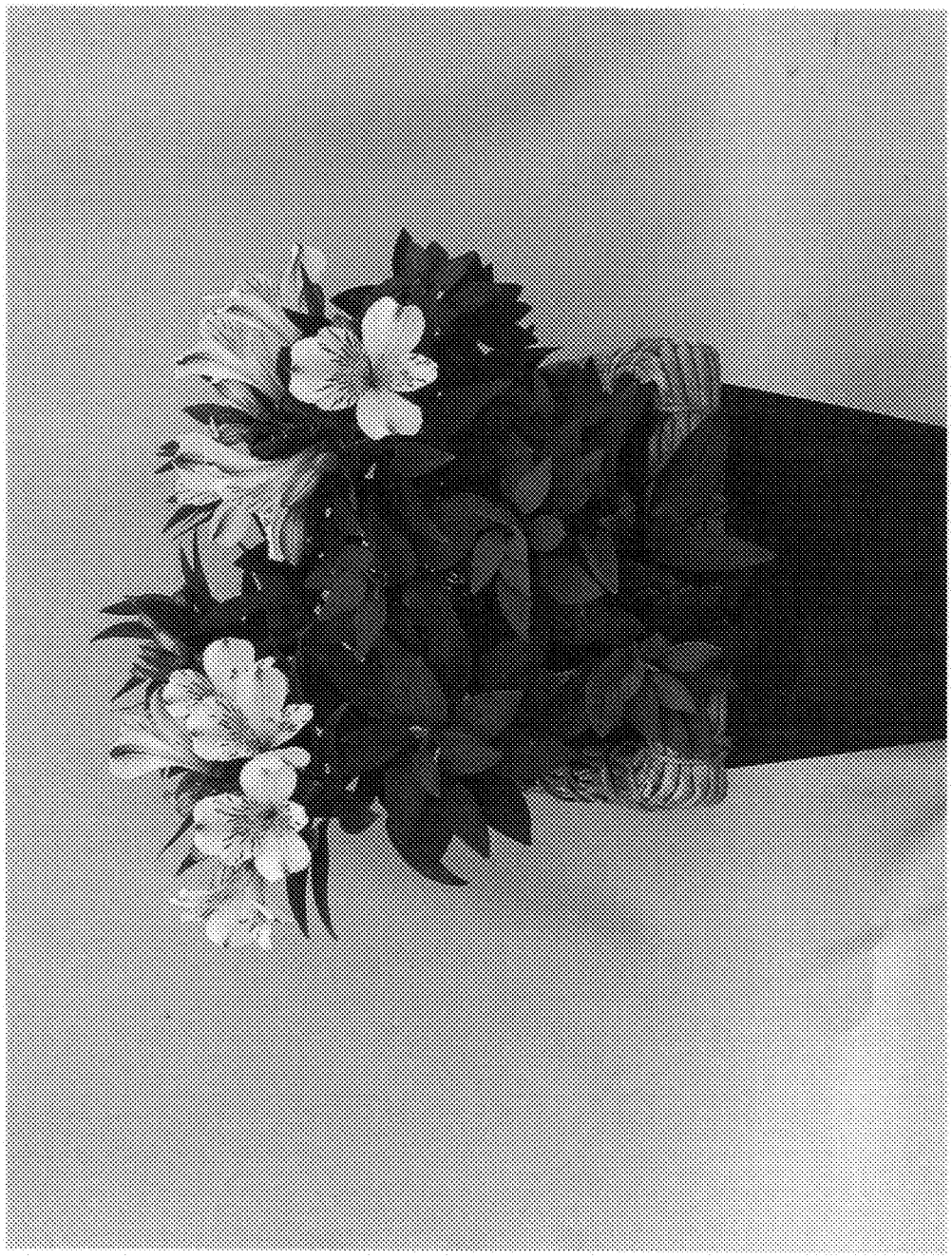

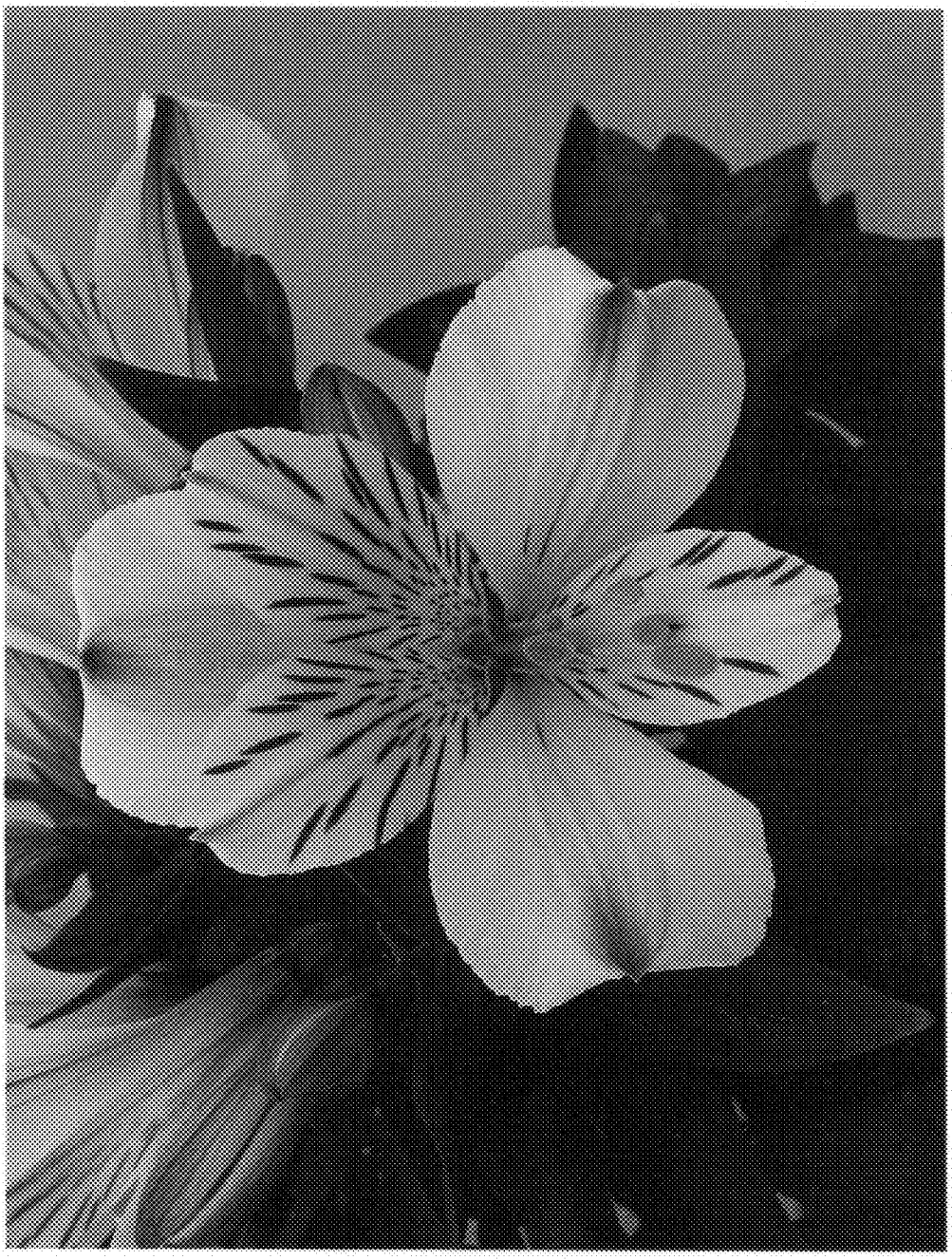

* * * * *